United States Patent
He et al.

(10) Patent No.: US 6,217,520 B1
(45) Date of Patent: Apr. 17, 2001

(54) DIAGNOSTIC MEDICAL ULTRASOUND SYSTEM AND METHOD FOR OBJECT OF INTEREST EXTRACTION

(75) Inventors: Anming He, San Jose; Joan C. Main, Mountain View, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/204,662

(22) Filed: Dec. 2, 1998

(51) Int. Cl.$^7$ .................................................. A61B 8/00
(52) U.S. Cl. ............................................................. 600/467
(58) Field of Search ................................. 600/437, 447, 600/449, 443; 382/128; 606/130

(56) References Cited

U.S. PATENT DOCUMENTS

| | | |
|---|---|---|
| 5,322,067 | 6/1994 | Prater et al. . |
| 5,526,812 | * 6/1996 | Dumoulin et al. ................. 606/130 |
| 5,570,430 | * 10/1996 | Sheehan et al. .................... 382/128 |
| 5,734,739 | * 3/1998 | Sheehan et al. .................... 382/128 |
| 5,806,521 | * 9/1998 | Morimoto et al. .................. 600/447 |

OTHER PUBLICATIONS

Karl Schwartz, MD et al., "Quantitative Left Ventricular Volume and Ejection Fraction by 3D Contrast Harmonic Color Doppler Left Ventriculography Compared to Equilibrium Gated Radionuclide Ventriculography", University of Rochester Echo, 22 pages (Jan. 22, 1998).

Acuson, "128XP The Value of Vision Cardiovascular Applications User Manual", 7 pages, (Nov. 1995).

Scott E. Umbaugh, "Computer Vision and Image Processing a Practical Approach Using CVIPtools", Prentice Hall PTR, pp. 92–95 and 133–136, (1998).

K.Q. Schwartz et al., "Left Ventricular Volume and Ejection Fraction by Three–Dimensional Harmonic Colour Doppler Contract Left Ventriculography compared to Equilibrium Radionuclide Angiography," Abstract No. 2080, "Quantitative Assessment of Left Ventricular Volumes and Function by Three Dimensional Echocardiography", 1 page.

* cited by examiner

Primary Examiner—Marvin M. Lateef
Assistant Examiner—Maulin Patel
(74) Attorney, Agent, or Firm—Brinks Hofer Gilson & Lione (57) ABSTRACT

The preferred embodiments include a diagnostic medical ultrasound system and method for object of interest extraction. Unlike some extraction techniques, the preferred embodiments do not require the user to perform the time consuming task of manually tracing the border of the object of interest. Further, unlike some automatic border detection techniques, the preferred embodiments produce an accurate border of an object of interest even if the object of interest is connected to neighboring anatomy with similar properties.

31 Claims, 5 Drawing Sheets

Microfiche Appendix Included
(1 Microfiche, 15 Pages)

DIAGNOSTIC MEDICAL ULTRASOUND SYSTEM AND METHOD FOR OBJECT OF INTEREST EXTRACTION

MICROFICHE APPENDIX

This application includes one microfiche appendix containing 1 microfiche with a total of 15 frames.

BACKGROUND

Quantification of ultrasound images often requires the identification of a border of an object of interest in the ultrasound image. For example, the left ventricle endocardial border often needs to be identified for quantification of left ventricle ejection fraction and left ventricle volume. Typically, a user manipulates on-screen cursors to manually trace the border on an ultrasound image.

New ultrasound imaging modalities, such as tissue harmonic imaging, contrast agent imaging, and intracardiac imaging, can provide better delineation between the different objects in the imaging region as compared to traditional B-mode gray-level and CD-mode color ultrasound images. For example, harmonic color-Doppler imaging with contrast agent enhancement has been shown to provide good blood pool-border delineation. As described in "Quantitative Left Ventricular Volume and Ejection Fraction by 3D Contrast Harmonic Color Doppler Left Ventriculography Compared to Equilibrium Gated Radionuclide Ventriculography," Schwartz, Bezante, Chen, and Villa, images acquired from the apical views of the left ventricle using this imaging modality produce vivid endocaridal delineation that can be used to accurately measure left ventricle volumes and left ventricle ejection fraction.

Even with the use of new ultrasound imaging modalities to improve the delineation between different objects in the imaging region, time-consuming manual border tracing is still widely used due to the lack of robust automatic border detection techniques. One of the difficulties encountered in existing techniques is that the object of interest in the imaging region is not sufficiently isolated from neighboring anatomy with similar properties. For example, the border of part of the right ventricle is sometimes identified as part of the border of the left ventricle. Additionally, the accuracy of these automatically-generated borders is often not sufficient for quantification applications that depend on a precise boundary.

Accordingly, there is a need for a diagnostic medical ultrasound system and method for object of interest extraction that will overcome the problems described above.

SUMMARY

The present invention is defined by the following claims, and nothing in this section should be taken as a limitation on those claims.

By way of introduction, the preferred embodiments described below include a diagnostic medical ultrasound system and method for object of interest extraction. Unlike some extraction techniques, the preferred embodiments do not require the user to perform the time consuming task of manually tracing the border of the object of interest. Further, unlike some automatic border detection techniques, the preferred embodiments produce an accurate border of an object of interest even if the object of interest is connected to neighboring anatomy with similar properties.

The preferred embodiments will now be described with reference to the attached drawings.

DETAILED DESCRIPTION OF THE PRESENTLY PREFERRED EMBODIMENTS

Figure 1:
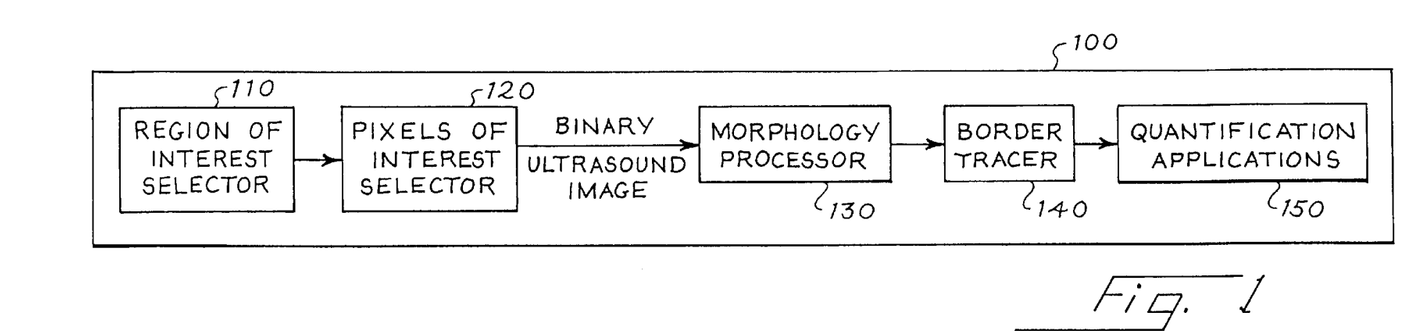
FIG. 1 is a block diagram of a diagnostic medical ultrasound system of a preferred embodiment.

Turning now to the drawings, FIG. 1 is a block diagram of a diagnostic ultrasound image system 100 of a preferred embodiment. Diagnostic ultrasound image systems include, but are not limited to, ultrasound image review stations and ultrasound image acquisition devices. Of course, the diagnostic ultrasound image system 100 may comprise components in addition to the ones shown in FIG. 1. Many, if not all, of these components may depend upon the particular system used and are, therefore, not shown in FIG. 1.

As shown in FIG. 1, the diagnostic ultrasound image system 100 comprises a region of interest selector 110, a pixels of interest selector 20, a morphology processor 130, a border tracer 140, and quantification applications 150. It is preferred that the components shown in FIG. 1 be implemented with software and that the diagnostic ultrasound image system 100 comprise the necessary hardware (such as a CPU) to execute the software. Of course, any appropriate software language and any appropriate hardware, analog or digital, can be used. Additionally, all of the functionality can be implemented exclusively with hardware. Appendix 1 contains a listing of the computer code of one presently preferred embodiment.

Figure 2:
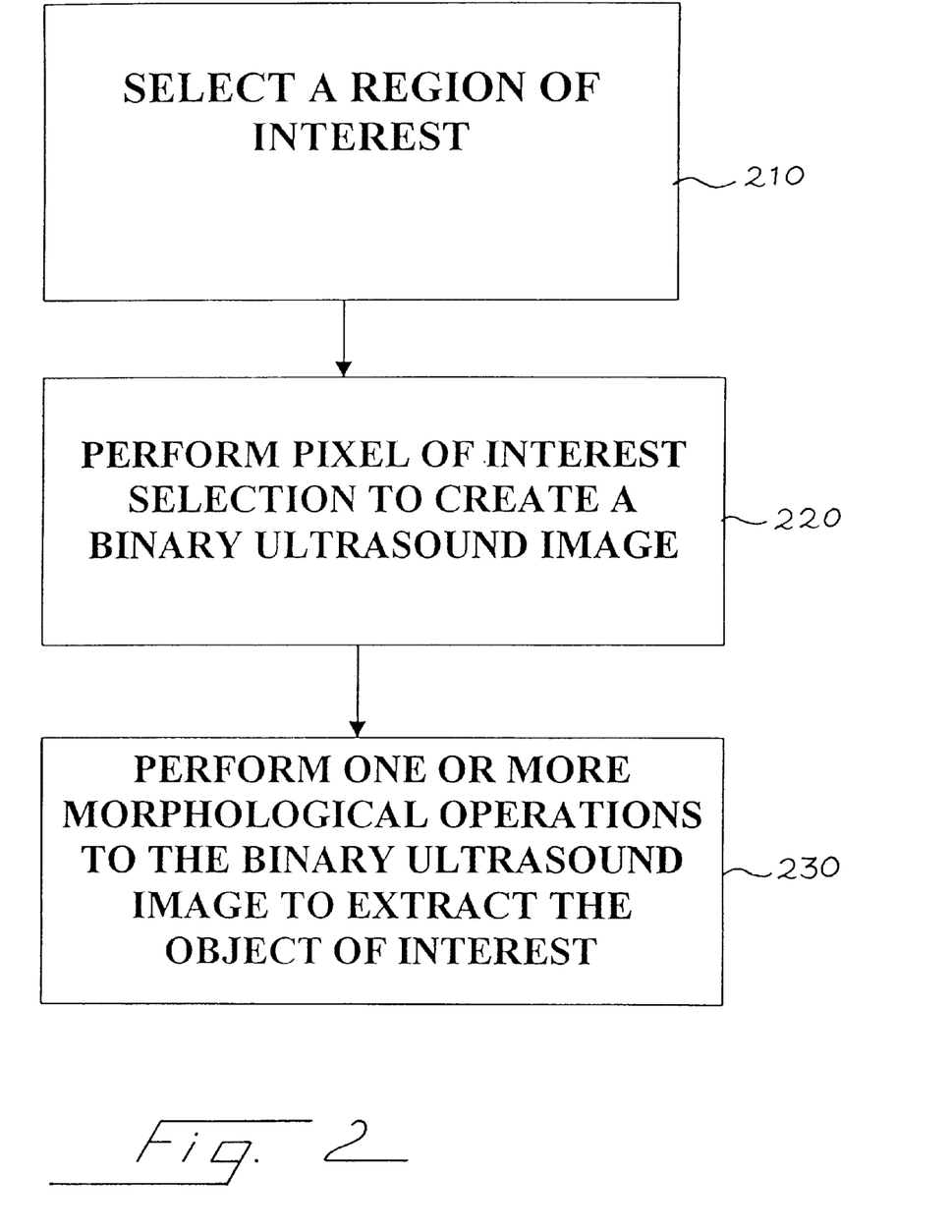
FIG. 2 is flow chart of a preferred method of extracting an object of interest from an ultrasound image.

FIG. 2 is a flow chart of a method of a preferred embodiment for using the diagnostic medical ultrasound system 100 of FIG. 1 to extract an object of interest in an ultrasound image. As shown in FIG. 2, this method comprises the steps of selecting a region of interest (210), performing pixels of interest selection to create a binary ultrasound image (220), and performing one or more morphological operations to the binary ultrasound image to extract the object of interest (230). Once the object of interest has been extracted, quantification operations can be performed on the extracted object.

Figure 3A:
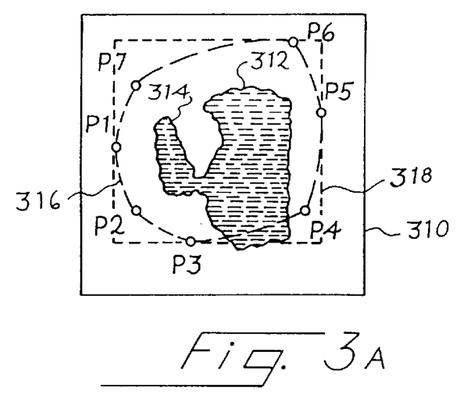
FIGS. 3A–3F are illustrations of an ultrasound image that is processed by the preferred method shown in FIG. 2.

These steps will be described in further detail below in reference to FIGS. 3A–F, which show the transformation of an ultrasound image processed by this preferred method. As shown in FIG. 3A, the ultrasound image 310 comprises the left ventricle 312 and part of the right ventricle 314. It is preferred that the ultrasound image be acquired with an ultrasound imaging modality such as tissue harmonic imaging, contrast agent imaging, contrast harmonic color Doppler, or intracardiac imaging. If a conventional automatic border detection technique were used to identify the border of this image, part of the right ventricle 314 may be included in the border of the left ventricle 312, resulting in inaccurate quantification calculations. The method shown in FIG. 2 will be illustrated below with reference to FIG. 3 to illustrate how this method can be used to extract the object of interest and properly identify its border.

Selecting a Region of Interest (210)

As shown in FIG. 2, the first step in the object of interest extraction process is to select a region of interest in the ultrasound image. One or more regions of interest can be selected. Multiple regions of interest can be selected so that multiple images can either share one region of interest or can be grouped with a number of regions of interest and a single region of interest shared within each group. In one preferred embodiment, the region of interest is automatically selected around the entire ultrasound image. In another preferred embodiment, the region of interest is manually selected by the user. For example, if the user desires only part of the ultrasound image to be processed, he can select a region of interest that is smaller than the entire ultrasound image.

In the preferred embodiment shown in FIG. 3A, a user manually selects points P1–P7 around the displayed object of interest (i.e., the left ventricle 312) using a user interface such as a trackball or mouse. The user needs only to quickly select points on the image to enclose the object of interest and does not need to carefully and slowly trace the border of the object. A region of interest polygon 316 connects points P1–P7 in the order that they were selected. Here, the region of interest polygon 316 encloses the left ventricle 312 as well as part of the right ventricle 314. The smallest rectangle ("the region of interest rectangle 318") that contains the region of interest polygon is then identified, and a new image is formed that only includes pixels inside the region of interest rectangle 318. The pixels in this new image have the same pixel values as the original image.

Performing Pixel of Interest Selection to Create a Binary Ultrasound Image (220)

Once the region of interest has been selected, pixels of interest inside the region of interest are then selected to create a binary ultrasound image. As used herein, the term "binary ultrasound image" refers to an ultrasound image that has only two pixel values (e.g., "0" and "1"). It is important to note that the use of "0" and "1" can be interchanged.

Various pixel of interest selection techniques can be applied depending on the image and user interest. For gray-level ultrasound images, upper and lower threshold values ranging from 0–255 can be selected by the user or can be set as default values. In one preferred embodiment, all of the pixels inside the region of interest polygon 316 that have a value above or the same as the lower threshold and below the upper threshold are set to "1", and all other pixels inside the region of interest rectangle 318 are set to "0". The result of this pixel of interest selection in shown in FIG. 3B. This method of thresholding is described in U.S. Pat. No. 5,322,067.

For color ultrasound images, a color-thresholding technique can be applied to set all the pixels that have certain color levels and reside inside the region of interest polygon 316 to "1" and the others "0". In one thresholding technique, the pixels inside the blood pool volume of a color-Doppler ultrasound image are isolated by two pixel masks. One pixel mask is a gray-pixel-elimination mask that is set by thresholding the difference between the sum of the R, G, and B pixel values over three times of the minimum among the three on each pixel in the image. The other pixel mask is a flash pixel mask that eliminates the color-pixels generated by high amplitude, low velocity tissue movements. This mask is set by thresholding the maximum of the R, G, and B values on each color pixel. This thresholding method is particularly accurate on harmonic flow color-Doppler images in velocity or velocity-variance mode with contrast agent enhancement that provides more color pixels inside the blood pool with the loss-of-coherence effects generated by harmonic generating bubble destruction caused by the ultrasound pulses for generating color-Doppler images. When the ultrasound system has separate image planes for B-mode images, scale-annotation, and color-Doppler mode image, this thresholding can be done on the color-Doppler image plane without a gray pixel mask.

Of course, other color-thresholding techniques can be used. In one alternate color-thresholding technique, the thresholding mask is set by thresholding velocity and variance directly prior to color mapping. Another technique is based on B-mode gray-level thresholding but uses the Doppler-flow color pixels to adjust the threshold level. The first mask is set by including all the pixels that have gray levels less than a certain threshold, and the second mask is set by including all the pixels that have color. These two masks are then OR-ed together. Yet another thresholding technique is based on B-mode gray level plus the color level in Doppler tissue imaging. Pixels that have both low gray level and low color level belong to the blood pool volume. Thresholding on these levels generates a mask to isolate the blood pool volume.

Of course, other thresholding techniques can be used, such as those described in U.S. patent application Ser. No. 08/753,999 filed Dec. 4, 1996 and U.S. patent application Ser. No. 08/916,590 filed Aug. 22, 1997, both of which are assigned to the Assignee of the present patent application and are hereby incorporated by reference.

Figure 3B:
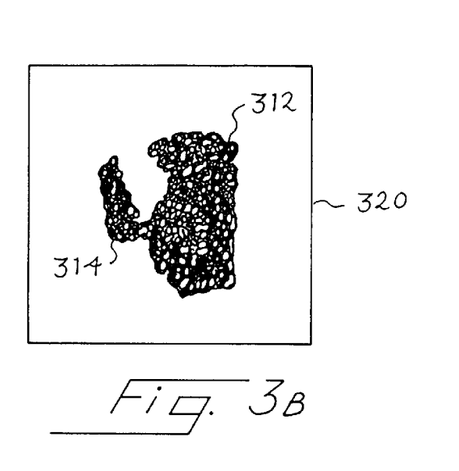

Regardless of the pixel of interest selection technique used, the result is a binary ultrasound image 320 (see FIG. 3B). Of course, if a binary image is originally presented to the diagnostic ultrasound image system 100, the step of selecting pixels of interest to create a binary image need not be performed. As shown in FIG. 3B, pixels outside the region of interest polygon 316 are set to 0, and pixels inside the region of interest polygon 316 are set to 1. The binary ultrasound image 320 contains pixels belonging to the left ventricle 312 as well as the right ventricle 314. As described below, the morphology processor 130 can be used to extract a specific object of interest (e.g., the left ventricle 312).

Performing Morphological Operations to the Binary Ultrasound Image (230)

As mentioned above, the morphology processor 130 can be used to extract a specific object of interest (e.g., the left ventricle 312). Morphological image processing is a branch of nonlinear image processing and analysis developed by Georges Matheron and Jean Serra in the 1980's that concentrates on the geometric structure within an image. By smoothing object outlines, filling small holes, and eliminating small projections, morphology simplifies a segmented image to facilitate the search for objects of interest. Morphological image processing is described in "Computer Vision and Image Processing: A Practical Approach Using CVIPtools," Scott E. Umbaugh (Prentice Hall 1998), which is hereby incorporated by reference. In the image example shown in FIG. 3B, part of the right ventricle 314 is connected to the left ventricle 312, and each of these objects contain holes or cavities with the objects. Three morphological processes—dilation, erosion, and selection—will be used to fill the holes in the two objects, separate the two objects, and select the object of interest, respectively.

Figure 3C:
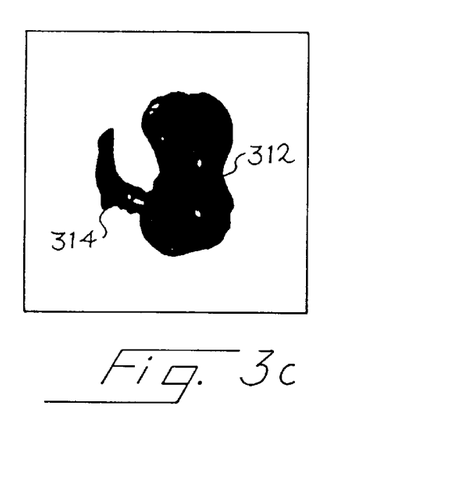
Figure 4:
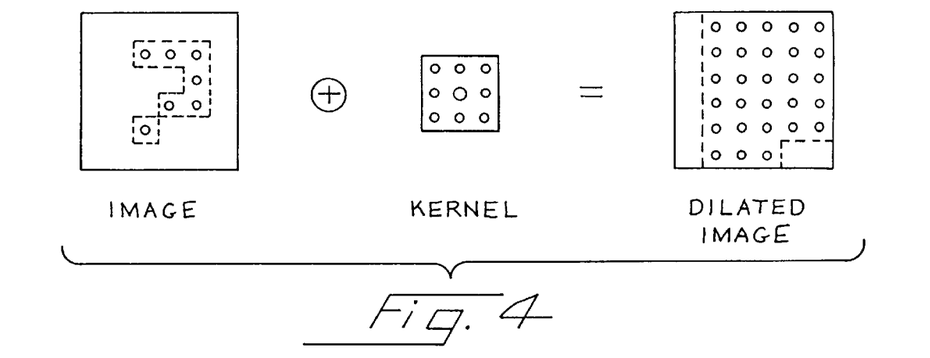
FIG. 4 is an illustration of a preferred method of dilating an ultrasound image.

When the morphology processor 130 receives the binary ultrasound image, it first dilates the image (230). As shown in FIG. 4, dilation adds pixels to an image wherever nonzero pixels in the image intersect the nonzero pixel in the center of a dilation kernel image, whose size and shape can be designed to control the degree of dilation. As shown in FIG. 3C, dilating the image of FIG. 3B expands the image by filling in small holes and connecting diagonal objects, resulting in a more well-defined image.

Figure 3D:
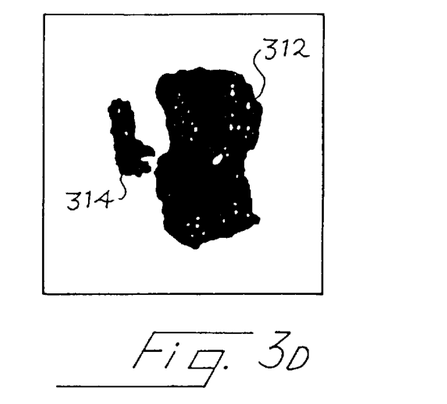
Figure 5:
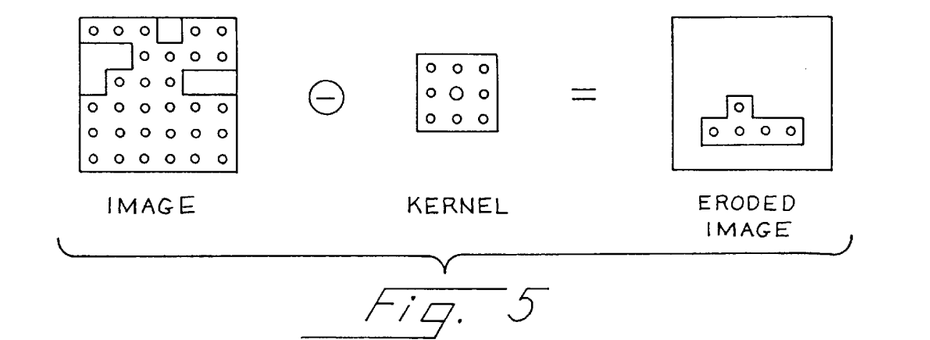
FIG. 5 is an illustration of a preferred method of eroding an ultrasound image.

Next, with the objects in the image being well-defined, the morphology processor 130 performs an erosion operation to break the links that connect the various objects in the image. The erosion operation deletes pixels from the image wherever a nonzero pixel in the image that does not have a nonzero neighborhood configuration that matches the nonzero configuration in the erosion kernel image, as shown in FIG. 5. As shown in FIG. 3D, eroding the image of FIG. 3C shrinks the image by etching away its boundaries, thereby breaking the link that formerly connected the right ventricle 314 with the left ventricle 312.

Finally, to extract the object of interest, the object of interest is first identified. The object of interest can be identified manually by the user (e.g., by the user selecting one or more points on the object of interest with a user interface). Alternatively, the object of interest can be automatically identified. For example, the largest object in the region of interest can be identified as the object of interest by determining which of the objects has the longest vertical or horizontal line running through it. Once the object of interest has been identified, the morphology processor 130 performs a selection operation to extract the identified object of interest from the region of interest.

Figure 3E:
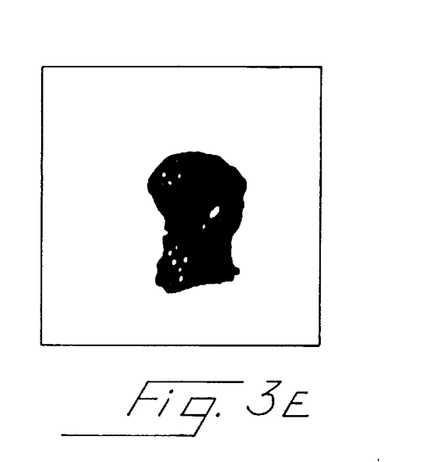
Figure 3F:
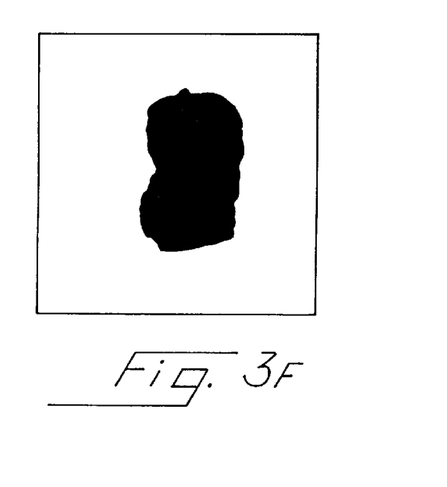
Figure 6:
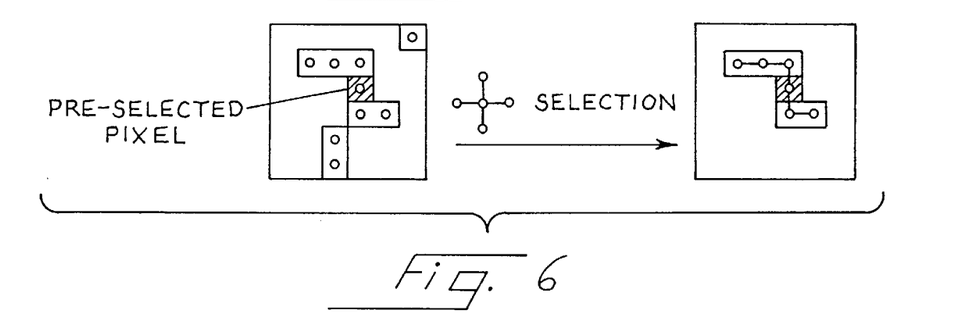
FIG. 6 is an illustration of a preferred method of extracting an object of interest in an ultrasound image by using a four-pixel selection operation.
Figure 7:
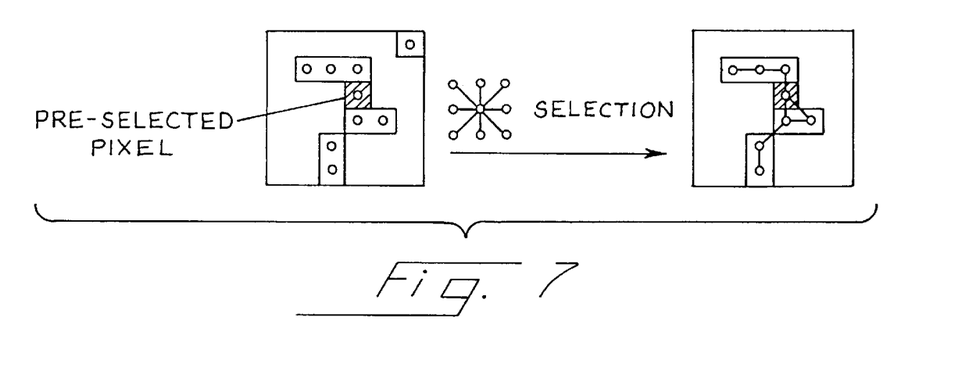
FIG. 7 is an illustration of a preferred method of extracting an object of interest in an ultrasound image by using an eight-pixel selection operation.

In the selection operation, nonzero pixels that are connected to a preselected set of pixels through other nonzero pixels are preserved. The connectivity can be tested with, for example, a four- or eight-connected neighbor criteria, as shown in FIGS. 6 and 7 respectively, to determine if a pixel belongs to the object of interest. If the object of interest is manually selected, connectivity with the preselected set of pixels can begin with a user select pixel in the object of interest. If the object of interest is automatically selected, connectivity with the preselected set of pixels can begin with the mid-point of the longest vertical or horizontal line that was used to determine the object of interest. The result of the selection process is the extracted object of interest, as shown in FIG. 3E. The extracted object of interest can then be dilated, preferably with a larger kernel than the one used in the first dilation step, to further fill the holes and smooth the border, as shown in FIG. 3F.

It is important to note that while the dilation, erosion, and selection processes were described above to identify and extract an object of interest in an ultrasound image, the dilation operation is not necessary if the object of interest is capable of being extracted without the dilation operation. This can occur, for example, if the ultrasound image is not very noisy. Additionally, the erosion operation is not necessary if the objects in the image are sufficiently separated to allow the selection process to extract only the object of interest.

Border Tracing and Quantification Applications

After the object of interest has been extracted from the region of interest, the border tracer 140 can trace the border of the extracted object of interest. For example, the border tracer 140 can trace the extracted object's boundary from the lowest (or highest) pixel on the object, moving up (or down) one pixel at a time, adding the left-most pixel on the left boundary and the right-most pixel on the right boundary until the highest (or lowest) pixel(s) on the object is reached.

The quantification applications 150 can be used to calculate the perimeter and area of the extracted object of interest. For example, if the coordinates of the i-th point on the left and right border of the extracted object of interest are $(x_{li}, y_i)$ and $(x_{ri}, y_i)$, respectively, and N is the number of points on the each border, $p_x$ is the corresponding physical length of a pixel in the x direction, and $p_y$ is the corresponding physical length of a pixel in the y direction, the perimeter and area of the extracted object of interest can be calculated as follows:

$$\text{Perimeter} = |x_{r_i} - x_{l_i}|p_x + |x_{r_n} - x_{l_n}|p_x +$$

$$\sum_{i=2}^{n} \sqrt{(x_{r_i} - x_{r_{i-1}})^2 p_x^2 + (y_i - y_{i-1})^2 p_y^2} +$$

$$\sum_{i=2}^{n} \sqrt{(x_{l_i} - x_{l_{i-1}})^2 p_x^2 + (y_i - y_{i-1})^2 p_y^2}$$

$$\text{Area} = \sum_{i=2}^{n} \frac{1}{2}[(x_{r_i} - x_{l_i}) + (x_{r_{i-1}} - x_{l_{i-1}})] \cdot (y_i - y_{i-1}) \cdot p_x p_y$$

$$= (\text{Number of pixels in the object}) \cdot p_x p_y$$

The volume of the extracted object of interest can also be calculated. When calculating the volume of the left ventricle when only one apical long-axis view plane image is available, the volume can be estimated by calculating the center of mass of the extracted object of interest and calculating the axis of least second momenta through the center of mass of the extracted object of interest, which corresponds to the line about which it takes the least amount of energy to spin an object of like shape or the axis of least inertia. The center of mass $(x_c, y_c)$ and the least second momenta (a) through the center of mass of the extracted object can be calculated as follows, where $I(x_i, y_i)$ equals 1 when pixel $(x_i, y_i)$ is inside the extracted area of interest and equals 0 otherwise:

$$x_c = \frac{1}{a}\sum_i x_i I(x_i, y_i)$$

$$y_c = \frac{1}{a}\sum_i y_i I(x_i, y_i)$$

where $a = \sum_i I(x_i, y_i)$ is the area $$\tan(2\theta) = \frac{\sum_i x_i y_i I(x_i, y_i)}{\sum_i y_i^2 I(x_i, y_i) - \sum_i x_i^2 I(x_i, y_i)}$$

Figure 8:
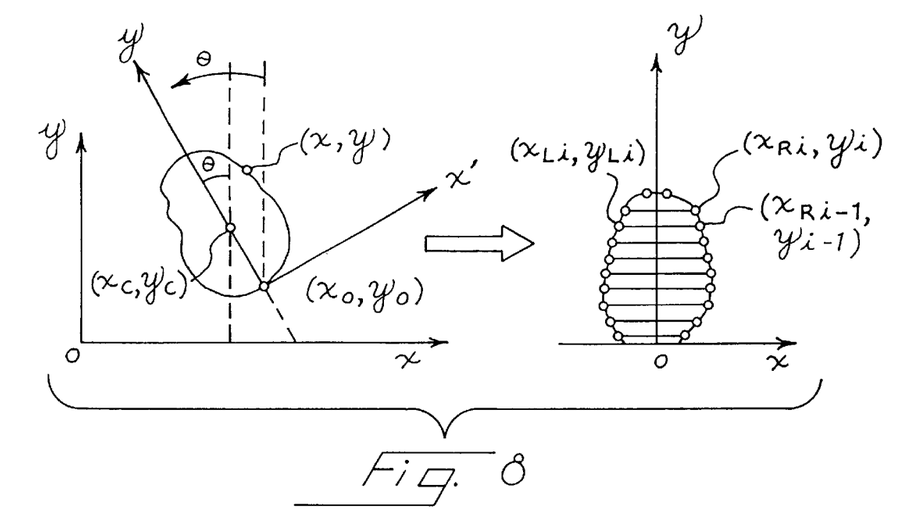
FIG. 8 are illustrations of an extracted area of interest of a preferred embodiment before and after its long axis is aligned with a vertical y axis.

In this technique, the axis of least second momenta can be assumed to be the long axis. Once the long axis is found, it can be aligned with the vertical y axis and the border curve can be resampled, as shown in FIG. 8. The rotational volume around the long axis can be calculated as follows:

$$\text{Volume} = \sum_i \pi \left[\frac{(x_{r_i} - x_{l_i})}{2}\right]^2 \cdot (y_i - y_{i-1})$$

Figure 9:
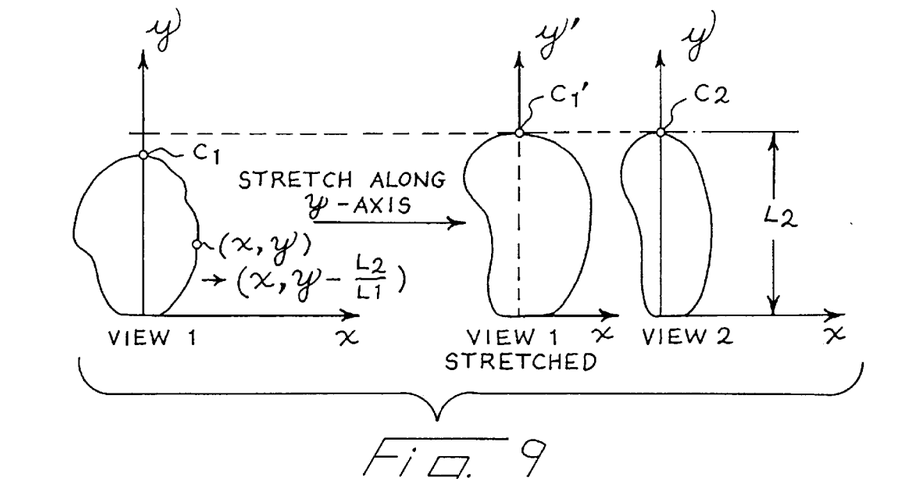
FIG. 9 are illustrations of extracted areas of interest of a preferred embodiment in which a border curve of the extracted area of interest with a shorter long axis is rescaled so the border curves of the extracted areas of interest have the same long axis length.
Figure 10:
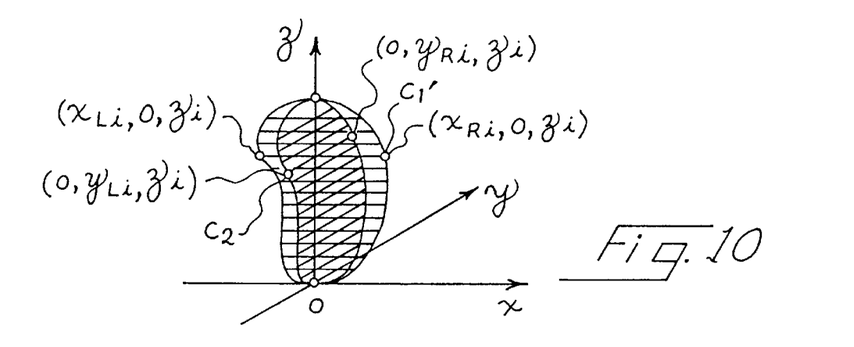
FIG. 10 is an illustration in which one of the border curves of FIG. 9 is placed on the XZ-plane, and the other is placed on the YZ-plane.

When two images are acquired on the same apical view location but with −90 degree rotation, a more accurate volume can be derived from them. After the long axis is aligned with the vertical y axis as described above, the length of the long axis in both images is calculated, and the border curve in the image with shorter long axis is rescaled so the two border curves have the same long axis length (see FIG. 9). Then, one border curve is placed on the XZ-plane, and the other is placed on the YZ-plane (see FIG. 10). The volume can then be calculated using Simpson's volume, which is described in "Left Ventricular Volume from Paired Biplane Two-Dimensional Exhocardiography" Schiller, Nelson B., M.D., H. Acquatella, T. A. Ports, et al. 1979 Circulation 60 (3):547–555, hereby incorporated by reference, and is reproduced below:

$$\text{Volume} = \sum_i \pi \frac{(x_{r_i} - x_{l_i})}{2} \cdot \frac{(y_{r_i} - y_{l_i})}{2} \cdot (z_i - z_{i-1})$$

Figure 11:
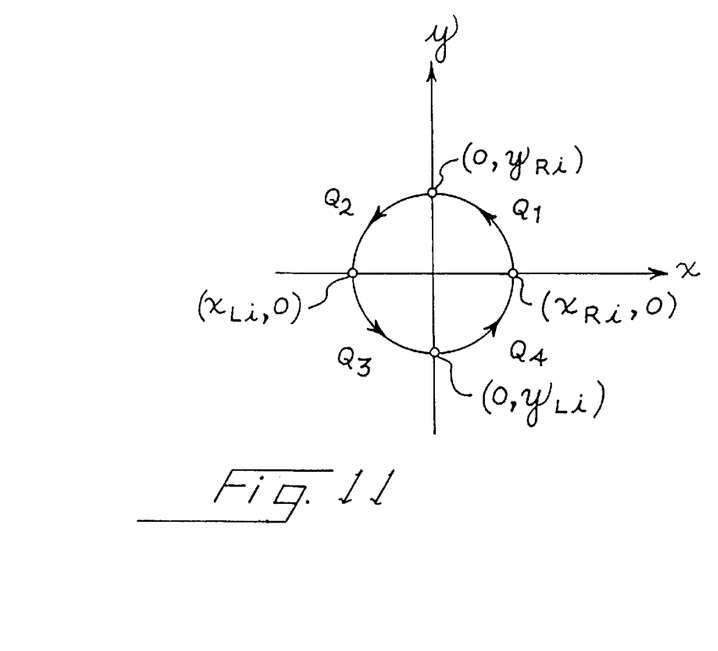
FIG. 11 is an illustration of how interpolation between four intersection points of a border curve using four elliptic arcs can be performed.

To display the volume surface, the following technique can be used. First, on each z-plane on the integer z-grid, interpolation between the four intersection points of the border curve with this plane using four elliptic arcs can be performed. With reference to FIG. 11, these calculations can be performed as follows:

$$Q_1: \frac{x^2}{x_{r_i}^2} + \frac{y^2}{y_{r_i}^2} = 1, \quad x \geq 0 \text{ and } y \geq 0$$

$$Q_2: \frac{x^2}{x_{l_i}^2} + \frac{y^2}{y_{r_i}^2} = 1, \quad x \leq 0 \text{ and } y \geq 0$$

$$Q_3: \frac{x^2}{x_{l_i}^2} + \frac{y^2}{y_{r_i}^2} = 1, \quad x \leq 0 \text{ and } y \leq 0$$

$$Q_4: \frac{x^2}{x_{r_i}^2} + \frac{y^2}{y_{l_i}^2} = 1, \quad x \geq 0 \text{ and } y \leq 0$$

Figure 12:
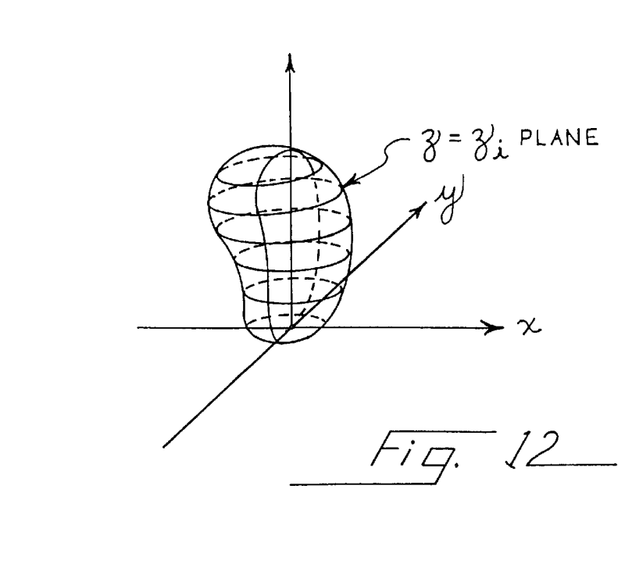
FIG. 12 is an illustration of how a wire frame surface can be displayed from the interpolation used in FIG. 11.

The resultant wire frame surface can be displayed using standard 3D wire frame display techniques to give the user visual information of the left ventricle, as shown in FIG. 12.

When a set of images in the same points of the cardiac cycle are acquired sequentially for each apical view, one region of interest is shared for all the images in the same view at the same point of cardiac cycles. For example, if a set of images in the apical 4-chamber (A4C) view is acquired with an image acquisition trigger set at the end of systole (ES) and another one set at the end of diastole (ED), the same number of images with the same triggers are acquired in the apical 2-chamber (A2C) view. In this situation, four regions of interest are used as follows: ES in A4C, ES in A2C, ED in A4C, ED in A2C.

Each ES in A4C images can be combined with the corresponding ES in A2C images to calculate left ventricle volume at ES and each ED in A4C image with the corresponding ED in A2C image for left ventricle volume at ED using the volume calculation based on two images described above. The left ventricle volumes at ES can be averaged to get an ES averaged volume, and the left ventricle volumes at ED can be averaged to get an ED averaged volume. Each individual ES (or ED) volume can then be compared with the corresponding average. If the difference is more than 10% of the average volume, for example, the specific volume can be removed from the group. The remaining volume in the group can then be averaged again to give the Adjusted average volumes—ED LV volume and ES LV volume. The left ventricular ejection fraction (LVEF) can be calculated using the formula: LVEF–[(ED LV Volume)–(ES LV Volume)]/(ED LV Volume).

Lastly, a method for displaying a diagnostic medical ultrasound image and associated quantification results can be performed in which the results of a quantification operation (such as the border tracing and perimeter, area, and volume calculations described above) can be simultaneously displayed with extracted object of interest and/or the ultrasound image from which the object of interest was extracted. In one preferred embodiment, the display monitor is divided into quadrants. One quadrant displays the extracted object, and the other three quadrants display the results of the quantification operations performed on the extracted object of interest.

It is intended that the foregoing detailed description be understood as an illustration of selected forms that the invention can take and not as a definition of the invention. It is only the following claims, including all equivalents, that are intended to define the scope of this invention.

What is claimed is:

1. A method for extracting an object of interest of a diagnostic medical ultrasound image, the method comprising:
    (a) selecting a region of interest of the ultrasound image;
    (b) selecting pixels of interest in the region of interest to create a binary ultrasound image;
    (c) dilating the binary ultrasound image created in (b);
    (d) eroding the binary ultrasound image dilated in (c); and
    (e) performing a selection operation on the binary ultrasound image eroded in (d) to extract an object of interest.

2. The invention of claim 1, wherein (b) comprises selecting pixels of interest in the region of interest with a gray-level thresholding technique.

3. The invention of claim 1, wherein (b) comprises selecting pixels of interest in the region of interest with a color thresholding technique.

4. The invention of claim 1, wherein (e) comprises automatically performing a selection operation on the binary ultrasound image eroded in (d).

5. The invention of claim 1, wherein (e) comprises performing a selection operation on the binary ultrasound image eroded in (d) based on a user input.

6. A method for extracting an object of interest in a diagnostic medical ultrasound image, the method comprising:
    (a) selecting a pixel in the object of interest;
    (b) determining whether the pixel selected in (a) is connected to at least one other pixel in the object of interest in accordance with a pre-selected pixel pattern;
    (c) extracting the pixel in response to the pixel being connected to said at least one other pixel in the object of interest in accordance with the pre-selected pixel pattern; and
    (d) extracting the object of interest by repeating (a)–(c) for a plurality of pixels in the object of interest.

7. The invention of claim 6, wherein (a) comprises manually selecting a pixel in the object of interest.

8. The invention of claim 6, wherein (a) comprises automatically selecting a pixel in the object of interest.

9. A method for identifying and extracting an object from a plurality of objects in a diagnostic medical ultrasound image, the method comprising:
(a) identifying an object from a plurality of objects in a diagnostic medical ultrasound image;
(b) selecting a pixel in the identified object;
(c) determining whether the pixel selected in (b) is connected to at least one other pixel in the identified object in accordance with a pre-selected pixel pattern;
(d) extracting the pixel in response to the pixel being connected to said at least one other pixel in the identified object in accordance with the pre-selected pixel pattern; and
(e) extracting the object of interest by repeating (b)–(d) for a plurality of pixels in the identified object.

10. The invention of claim 9, wherein (a) comprises manually identifying the object of interest.

11. The invention of claim 9, wherein (a) comprises automatically identifying the object of interest.

12. The invention of claim 9, wherein (b) comprises manually selecting a pixel in the object of interest.

13. The invention of claim 9, wherein (b) comprises automatically selecting a pixel in the object of interest.

14. A method for identifying and extracting an object connected to at least one other object in a diagnostic medical ultrasound image, the method comprising:
(a) separating the object of interest from said at least one other object; then
(b) identifying the object of interest; and then
(c) extracting the object of interest.

15. The invention of claim 14, wherein (a) comprises:
(a1) determining whether a pixel in the diagnostic medical ultrasound image is connected to at least one other pixel in the identified object in accordance with a pre-selected pixel pattern; and
(a2) deleting the pixel in response to the pixel not being connected to said at least one other pixel in the identified object in accordance with the pre-selected pixel pattern.

16. The invention of claim 14, wherein (b) comprises manually identifying the object of interest.

17. The invention of claim 14, wherein (b) comprises automatically identifying the object of interest.

18. The invention of claim 14, wherein (c) comprises:
(c1) selecting a pixel in the identified object;
(c2) determining whether the pixel selected in (c1) is connected to at least one other pixel in the identified object in accordance with a pre-selected pixel pattern;
(c3) extracting the pixel in response to the pixel being connected to said at least one other pixel in the identified object in accordance with the pre-selected pixel pattern, and
(c4) extracting the identified object by repeating (c1)–(c3) for a plurality of pixels in the object of interest.

19. The invention of claim 1, 6, 9, or 14, further comprising tracing a border of the extracted object of interest.

20. The invention of claim 1, 6, 9, or 14, further comprising calculating a perimeter of the extracted object of interest.

21. The invention of claim 1, 6, 9, or 14, further comprising calculating an area of the extracted object of interest.

22. The invention of claim 1, 6, 9, or 14, further comprising calculating a volume of the extracted object of interest.

23. A method for calculating a volume of an extracted object of interest in a diagnostic medical ultrasound image, the method comprising:
(a) extracting an object of interest from a diagnostic medical ultrasound image;
(b) calculating a center of mass of the extracted object of interest;
(c) calculating an axis of least second momenta through the center of mass of the extracted object of interest; and
(d) calculating the rotational volume around the axis of least second momenta.

24. The invention of claim 23, wherein the extracted object of interest is a left ventricle of a heart and wherein the diagnostic ultrasound image is an apical long-axis view plane ultrasound image of a heart.

25. A method for calculating a volume of an extracted object of interest in a diagnostic medical ultrasound image, the method comprising:
(a) acquiring two diagnostic medical ultrasound images, one of said images being at a −90 degree rotation with respect to the other;
(b) extracting a respective object of interest from each of said images;
(c) placing a border curve of one object of interest on an XZ-plane;
(d) placing a border curve of another object of interest on an YZ-plane; and
(e) calculating a volume defined by the border curves placed on the XZ- and YZ-planes.

26. The invention of claim 25 further comprising calculating a respective axis of least second momenta for each image, the respective axes having different lengths; and rescaling the extracted object of interest having a short axis, said calculating and rescaling being performed between (b) and (c).

27. The invention of claim 25 further comprising:
(f) displaying a wire frame surface of the border curves placed on the XZ- and YZ-planes.

28. A method for calculating a volume of an extracted object of interest in a set of ultrasound images acquired in an apical 4-chamber view at the end of systole and at the end of diastole and in an apical 2-chamber view at the end of systole and at the end of diastole, the method comprising:
(a) extracting a left ventricle in each of said acquired images;
(b) calculate a left ventricle volume at end of systole; and
(c) calculate a left ventricle volume at end of diastole.

29. The invention of claim 28 further comprising:
(d) averaging the left ventricle volumes at end of systole and the left ventricle volumes at the end of diastole;
(e) comparing individual left ventricle volumes with the averages calculated in (d);
(f) removing an individual left ventricle volume in response to said individual left ventricle volume being more than a predetermined amount above the averages; and
(g) calculating a left ventricular ejection fraction.

30. A method for displaying a diagnostic medical ultrasound image and associated quantification results, the method comprising:
(a) extracting an object of interest from a diagnostic medical ultrasound image;
(b) performing at least one quantification operation to the extracted object of interest; and (c) simultaneously displaying the diagnostic medical ultrasound image and the results of at least one of the quantification operations performed in (b).

31. The invention of claim 30, wherein (c) comprises simultaneously displaying the diagnostic medical ultrasound in one quadrant of a monitor and the results of the quantification operations performed in (b) in the other three quadrants of the monitor.

* * * * *